United States Patent
Gan

(10) Patent No.: US 12,292,432 B1
(45) Date of Patent: May 6, 2025

(54) SOIL TESTING INSTRUMENT

(71) Applicant: Zhihua Gan, Guangdong (CN)

(72) Inventor: Zhihua Gan, Guangdong (CN)

( * ) Notice: Subject to any disclaimer, the term of this patent is extended or adjusted under 35 U.S.C. 154(b) by 0 days.

(21) Appl. No.: 18/401,218

(22) Filed: Dec. 29, 2023

(30) Foreign Application Priority Data

Dec. 14, 2023 (CN) .......................... 202323423474.0

(51) Int. Cl.
*G01N 33/24* (2006.01)
*G01N 35/00* (2006.01)

(52) U.S. Cl.
CPC ..... *G01N 33/246* (2013.01); *G01N 35/00871* (2013.01); *G01N 33/245* (2024.05); *G01N 35/00732* (2013.01); *G01N 2035/0091* (2013.01)

(58) Field of Classification Search
CPC ........... G01N 33/246; G01N 35/00871; G01N 35/00732; G01N 2033/245; G01N 2035/0091
See application file for complete search history.

(56) References Cited

U.S. PATENT DOCUMENTS

| | | | | |
|---|---|---|---|---|
| 8,593,152 | B2 * | 11/2013 | Laepple | G01R 27/20 324/509 |
| 8,812,007 | B2 * | 8/2014 | Hitt | A01G 25/167 370/335 |
| 9,322,817 | B2 * | 4/2016 | Williams | G01N 21/77 |
| 9,766,270 | B2 * | 9/2017 | Heydron | G01R 15/12 |
| 11,428,724 | B2 * | 8/2022 | Westbrook | F21V 13/04 |
| 2024/0053320 | A1 * | 2/2024 | Yu | G01N 33/246 |

FOREIGN PATENT DOCUMENTS

| | | | | |
|---|---|---|---|---|
| CN | 206514881 | U | * | 9/2017 |
| CN | 206583903 | U | * | 10/2017 |
| CN | 109799144 | A | * | 5/2019 |
| CN | 210199099 | U | * | 3/2020 |
| CN | 210742747 | U | * | 6/2020 |
| CN | 112198198 | A | * | 1/2021 |
| CN | 213516976 | U | * | 6/2021 |
| CN | 215678376 | U | * | 1/2022 |
| CN | 218098978 | U | * | 12/2022 |
| CN | 221302397 | U | * | 7/2024 |
| KR | 100773427 | B1 | * | 11/2007 |

* cited by examiner

Primary Examiner — Octavia Hollington

(57) ABSTRACT

A soil testing instrument includes a host unit and a tester. The tester is connected to the host unit through wireless communication. The wireless communication connection is configured to achieve wireless communication between the host unit and the tester. The host unit and the tester are connected through the wireless communication. After the tester is automatically matched with the host unit, the tester can transmit tested data to the host unit through the wireless communication. This achieves remote monitoring of the soil data, and a user does not need to monitor the tested data in real time, thus bringing convenience to the user when testing the soil data. The host unit can be connected to a plurality of testers simultaneously.

20 Claims, 7 Drawing Sheets

SOIL TESTING INSTRUMENT

CROSS-REFERENCE TO RELATED APPLICATIONS

The application claims priority of Chinese patent application NO. 2023234234740, filed on 2023 Dec. 14, which is incorporated herein by reference in its entireties.

TECHNICAL FIELD

The present disclosure relates to a testing instrument, and in particular, to a soil testing instrument, which is applied to the technical field of soil testing equipment.

BACKGROUND

A good soil environment is essential for growth of plants. Different plants or the same kind of plants have different needs for a soil environment at different growth stages. Users can timely be helped understand changes in basic conditions of soil by testing a light intensity value of an environment, a moisture content value, an ambient temperature, a PH value, fertility, nitrogen fertilizer, potash fertilizer, and phosphate fertilizer, and determine whether growth of plants in the soil is in urgent need of water, PH value, fertility, nitrogen fertilizer, potash fertilizer, phosphate fertilizer, and light. Timely obtaining of information of temperature changes in an environment for plant growth can prevent damage to the plants caused by sudden cooling and warming of the weather and ensure that the plants grow in a relatively ideal soil environment, thus increasing both production and income. Therefore, a soil testing instrument plays an important role in the growth process of the plants.

At present, most existing portable soil testing instruments include a host unit and a testing module which are integrated. For example, patent No. CN210323011U, entitled with soil testing instrument, includes a connecting rod. One end of the connecting rod is provided with a meter head, and the other end of the connecting rod is provided with a probe. That is, the host unit and the testing module are integrated. This integration of the host unit and the testing module is not convenient for users, and remote monitoring cannot be achieved. The users need to use this soil testing instrument in person. Real-time monitoring is required, which bothers the users.

SUMMARY

The present disclosure aims at the problems mentioned in the background section that a host unit and a testing module of a soil testing instrument in the prior art are integrated, which cannot achieve remote monitoring; users need to use this soil testing instrument in person; and real-time monitoring is required, which bothers the users. The present disclosure provides a soil testing instrument. The host unit and the tester are connected through the wireless communication. After the tester is automatically matched with the host unit, the tester can transmit tested data to the host unit through the wireless communication. This achieves remote monitoring of the soil data, and a user does not need to monitor the tested data in real time, thus bringing convenience to the user when testing the soil data. The host unit can be connected to a plurality of testers simultaneously.

The technical solution adopted by the present disclosure to solve the technical problem is as follows: A soil testing instrument, wherein the soil testing instrument includes a host unit and a tester; the tester is connected to the host unit through wireless communication; the wireless communication connection is configured to achieve wireless communication between the host unit and the tester.

Further, the wireless communication includes a signal transmitter and a signal receiver; the signal receiver is arranged on the host unit and is electrically connected to the host unit; the signal transmitter is arranged on the tester and is electrically connected to the tester; the data tested by the tester is transmitted to the signal receiver through the signal transmitter; the signal receiver transmits the received data to the host unit; and the host unit displays the tested data through a display screen of the host unit.

Further, both the signal transmitter and the signal receiver are antennas.

Further, the tester includes a tester main body, a first control circuit board, and a testing module; the first control circuit board and the signal transmitter are both arranged inside the tester main body; the testing module is arranged on the tester main body; the testing module and the signal transmitter are electrically connected to the first control circuit board; the host unit includes a host unit main body, a second control circuit board and the display screen; the display screen and the signal receiver and the second control circuit board are arranged inside the host unit main body; the display screen is arranged on one side of the host unit main body; the signal receiver and the second control circuit board are electrically connected to the second control circuit board; the first control circuit board acquires the tested data through the testing module; the tested data acquired by the first control circuit board is then transmitted to the signal receiver through the signal transmitter; and the signal receiver transmits the received tested data to the second control circuit board; the second control circuit board the received tested data to the display screen.

Further, the testing module includes one or more of a soil moisture testing unit and a light testing unit, a PH value testing unit, a fertility testing unit, a nitrogen fertilizer testing unit, a potash fertilizer testing unit, and a phosphate fertilizer testing unit.

Further, the soil moisture testing unit includes a testing probe; the testing probe is used to tests a soil moisture value, a soil PH value, a soil fertility content value, a soil nitrogen fertilizer content value, a soil potash fertilizer content value, and a soil phosphate fertilizer content value through the testing probe; the testing probe is arranged at one end of the tester main body; one end of the testing probe is configured to be inserted into soil, and the other end of the testing probe is electrically connected to the first control circuit board; and the end of the testing probe that is configured to be inserted into the soil is conical.

Further, the tester main body includes a shell, a base, a mounting column and a first storage power supply; the mounting column is vertically mounted on the base; the shell sleeves the mounting column; the shell is detachably covered at the base; and the first control circuit board and the first storage power supply are mounted on the mounting column. The first storage power supply is electrically connected to the first control circuit board.

Further, the light testing unit includes a photosensitive sensor; the photosensitive sensor is configured to test an ambient temperature; the photosensitive sensor is arranged inside the tester main body; and the photosensitive sensor is electrically connected to the first control circuit board.

Further, a first sliding chute and a second sliding chute are arranged on the base; both the first sliding chute and the second sliding chute are arranged on a side wall of the base;

a notch of the first sliding chute is formed towards the mounting column; the first sliding chute is communicated to the second sliding chute; one end of the second sliding chute is vertically arranged at one end of the first sliding chute away from the mounting column; the shell is provided with a convex block at one end close to the base; the convex block is arranged on an inner wall of the shell; when the shell is mounted on the base, the convex block slides from the first sliding chute into the second sliding chute; and then the shell is rotated to clamp the convex block in the second sliding chute.

Further, the host unit further includes a toggle button. When the host unit is connected to two or more testers, the toggle button can switch the tested data corresponding to the testers.

Beneficial effects of the present disclosure are as follows: The present disclosure provides a soil testing instrument, The host unit and the tester are connected through the wireless communication. After the tester is automatically matched with the host unit, the tester can transmit tested data to the host unit through the wireless communication. This achieves remote monitoring of the soil data, and a user does not need to monitor the tested data in real time, thus bringing convenience to the user when testing the soil data. The host unit can be connected to a plurality of testers simultaneously. When the testers are used for testing simultaneously, the user can observe tested data of different regions at any time through the host unit, which brings convenience to the user.

DETAILED DESCRIPTION OF THE EMBODIMENTS

In order to make the aims, technical solution and advantages of the present disclosure will be clearly, the present disclosure is further described below in combination with accompanying drawings and implementations. It should be understood that the specific embodiments described herein are intended only to explain the present disclosure and are not intended to define the present disclosure.

Referring to FIG. 1 to FIG. 8, the present disclosure provides a soil testing instrument. The soil testing instrument includes a host unit 1 and a tester 2. The tester 2 is configured to test data of a plant growth environment, such as an ambient temperature, soil humidity, light, a PH value, fertility, nitrogen fertilizer, potash fertilizer, or phosphate fertilizer. The tester 2 is connected to the host unit 1 through wireless communication. The wireless communication connection is configured to achieve wireless communication between the host unit 1 and the tester 2. That is, the host unit and the tester are connected through the wireless communication. After the tester is automatically matched with the host unit, the tester can transmit tested data to the host unit through the wireless communication. This achieves remote monitoring of the soil data, and a user does not need to monitor the tested data in real time, thus bringing convenience to the user when testing the soil data. The host unit can be connected to a plurality of testers simultaneously.

The wireless communication can be Bluetooth, a wireless local area network, mobile communication, radio frequency identification, infrared, satellite communication, radio broadcasting, and the like. The wireless communication in this embodiment uses one of the aforementioned technologies, that is, the wireless communication is the prior art, and how the wireless communication between the host unit and the tester is achieved will not be elaborated here.

Figure 1:
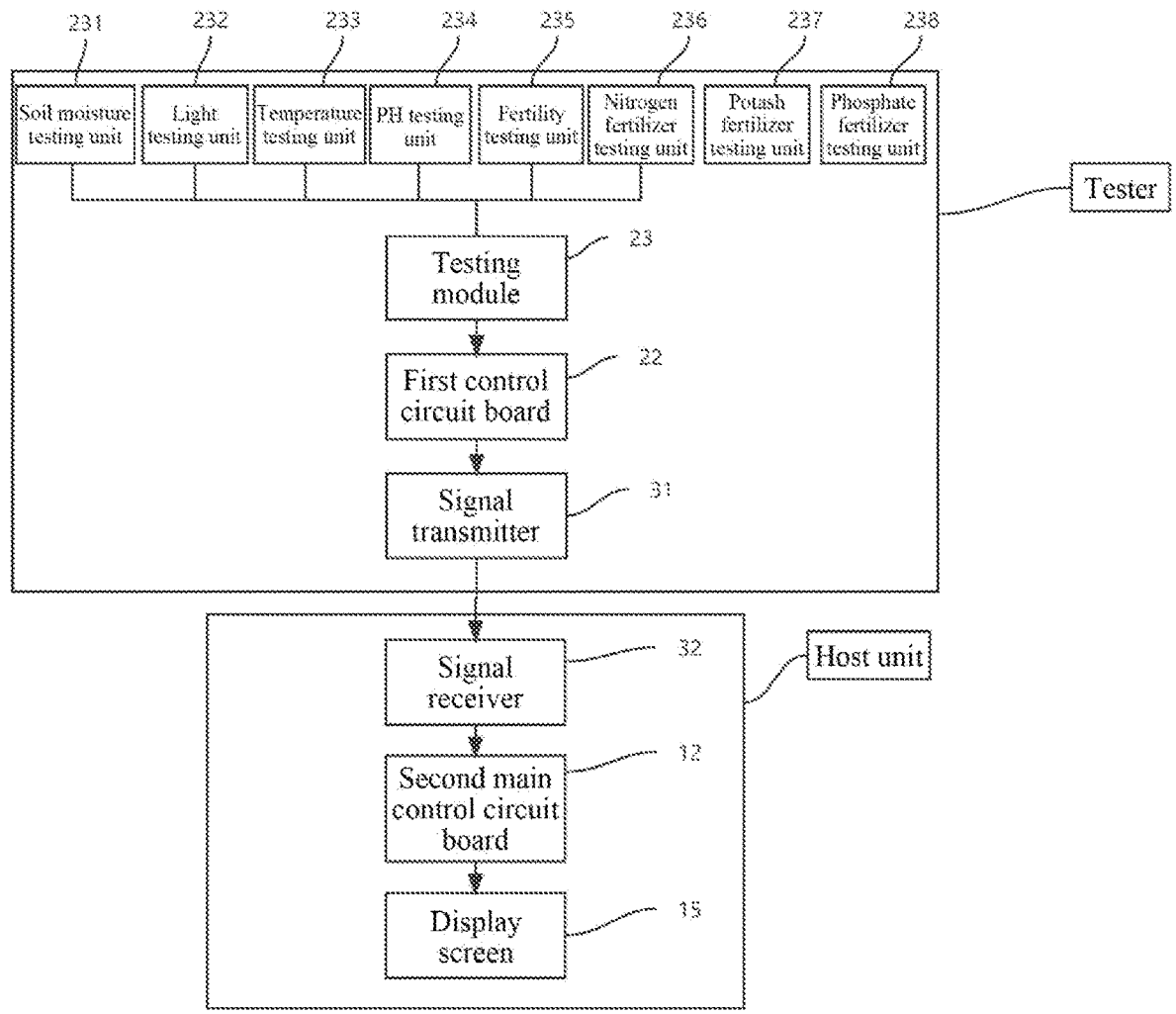
FIG. 1 is a flowchart of data transmission according to the present disclosure.
Figure 2:
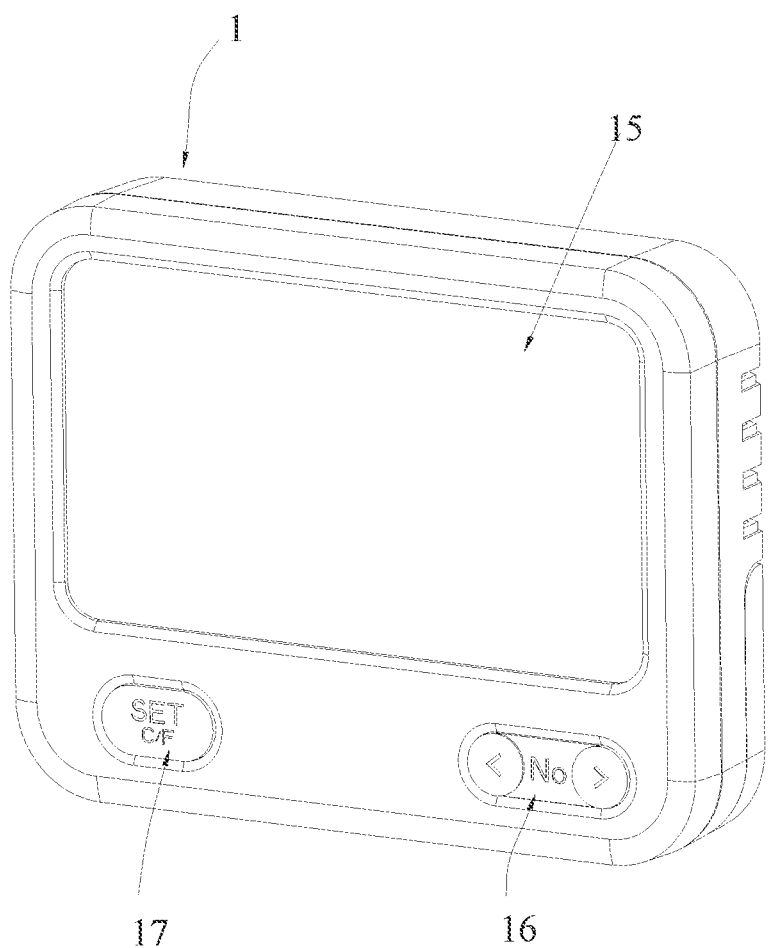
FIG. 2 is a three-dimensional diagram of a host unit according to the present disclosure.
Figure 4:
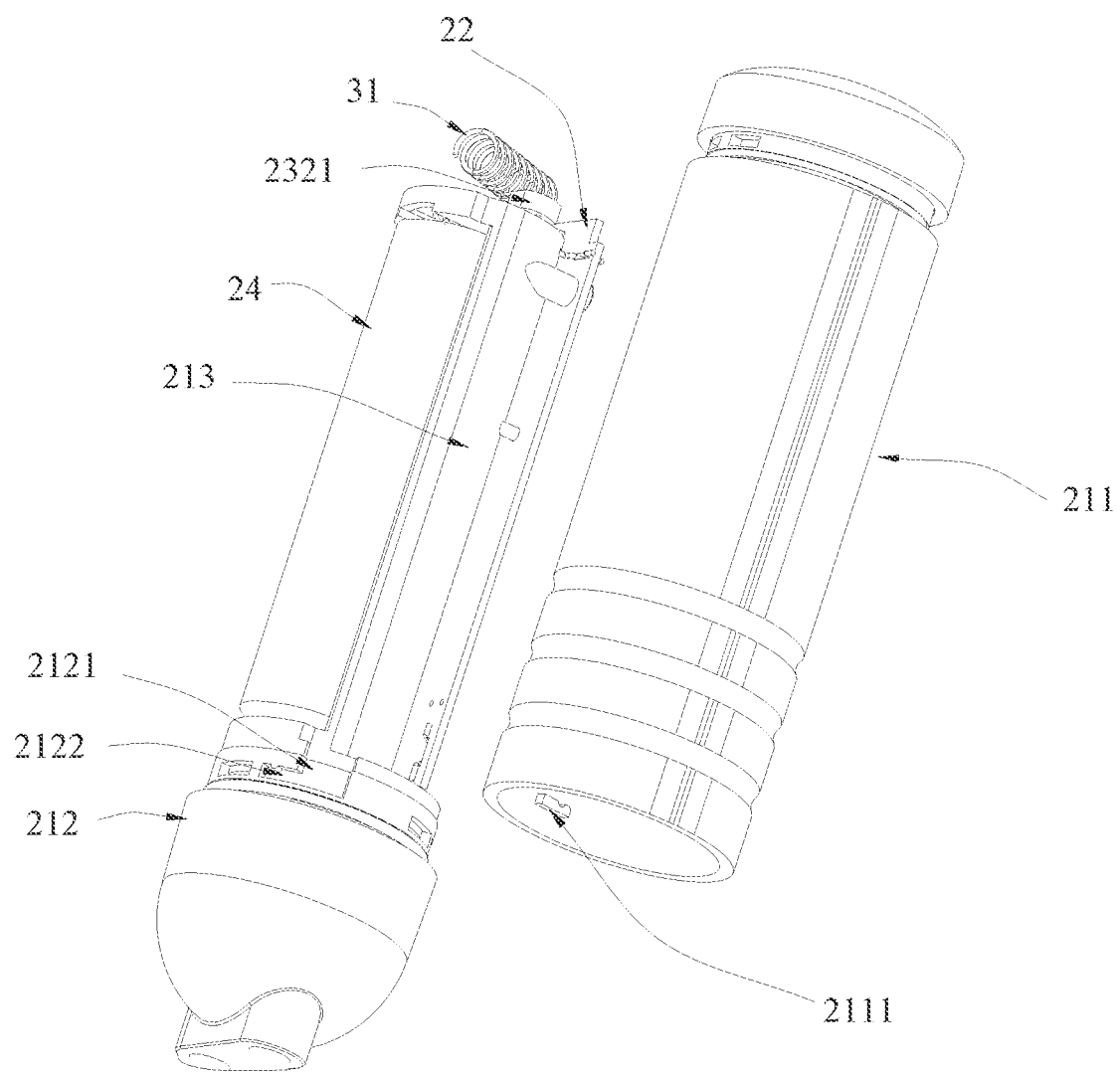
FIG. 4 is an exploded diagram of a tester according to the present disclosure.
Figure 6:
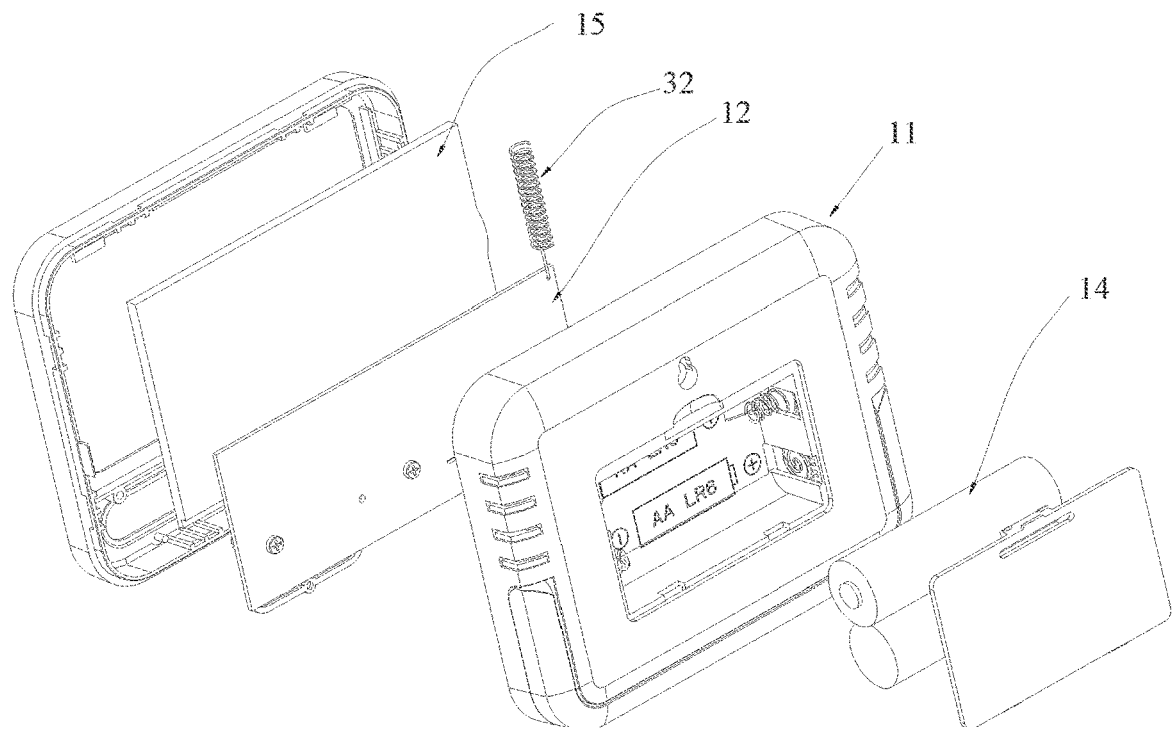
FIG. 6 is an exploded diagram of a host unit according to the present disclosure.

In this embodiment, as shown in FIG. 1, FIG. 4, and FIG. 6, the wireless communication includes a signal transmitter 31 and a signal receiver 32. The signal transmitter 31 is configured for signal transmission. The signal receiver 32 is configured to receive a signal transmitted by the signal transmitter. The signal receiver 32 is arranged on the host unit 1 and is electrically connected to the host unit 1. The signal transmitter 31 is arranged on the tester 2 and is electrically connected to the tester 2. Data tested by the tester 2 is transmitted to the signal receiver 32 through the signal transmitter 31. The signal receiver 32 transmits the received data to the host unit 1, and the host unit 1 displays the data through a display screen of the host unit. A transmitter is a device configured to convert an electrical signal into a wireless signal and transmit the wireless signal to a receiver. A receiver is a device that receives the wireless signal and converts the wireless signal into the electrical signal for outputting. That is, the signal transmitter 31 converts the data tested by the tester 2 into a wireless signal and transmits the wireless signal to the signal receiver 32. The signal receiver 32 converts the received wireless signal into the electrical signal and output the electric signal the host unit 1, so that the host unit can receive the data tested by the tester 2 and display the data on the display screen of the host unit. The transmitter and the receiver are both of the prior art, and the principles of the transmitter and receiver will not be further elaborated here.

In this embodiment, as shown in FIG. 4 and FIG. 6, both the signal transmitter 31 and the signal receiver 32 are antennas. The antennas are of the prior art and have lower costs compared to other transmitters and receivers, which can reduce the overall production cost of the soil testing instrument.

In this embodiment, as shown in FIG. 1, FIG. 4, and FIG. 6, the tester 2 includes a tester main body 21, a first control circuit board 22, and a testing module 23; the first control circuit board 22 and the signal transmitter 31 are both arranged inside the tester main body 21; the testing module 23 is arranged on the tester main body 21; the testing module 23 and the signal transmitter 31 are electrically connected to the first control circuit board 22; the host unit 1 includes a host unit main body 11 and a second control circuit board 12; the signal receiver 32 and the second control circuit board 12 are arranged inside the host unit main body 11; the signal receiver 32 and the second control circuit board 12 are electrically connected; the first control circuit board 22 acquires the tested data through the testing module 23; the tested data acquired by the first control circuit board 22 is then transmitted to the signal receiver 32 through the signal transmitter 31; and the signal receiver 32 transmits the received tested data to the host unit 1. The host unit displays the tested data of the testing module of the tester 2, so that it is convenient for the user to observe the tested data. The first control circuit board 22 in this embodiment is arranged on a first control circuit board panel 220 of the tester main body 21; and the first control circuit board panel 220 is arranged inside the tester main body 21. The second control circuit board in this embodiment is arranged on a second control circuit board panel 120 of the host unit, and the second control circuit board panel 120 is arranged inside the host unit body 11.

In this embodiment, as shown in FIG. 1, the testing module 23 includes one or more of a soil moisture testing unit 231, a light testing unit 232, a PH value testing unit 234, a fertility testing unit 235, a nitrogen fertilizer testing unit 236, a potash fertilizer testing unit 237, and a phosphate fertilizer testing unit 238. The soil moisture testing unit mainly tests soil moisture. In a plant growth process, the soil moisture plays an important role in plants. If the soil moisture is unreasonable, the plants cannot grow fast, and the plants may even die of drought and flood. Therefore, in this embodiment, the soil moisture testing unit 231 is arranged to improve the practicality of the soil testing instrument in the present disclosure.

Figure 3:
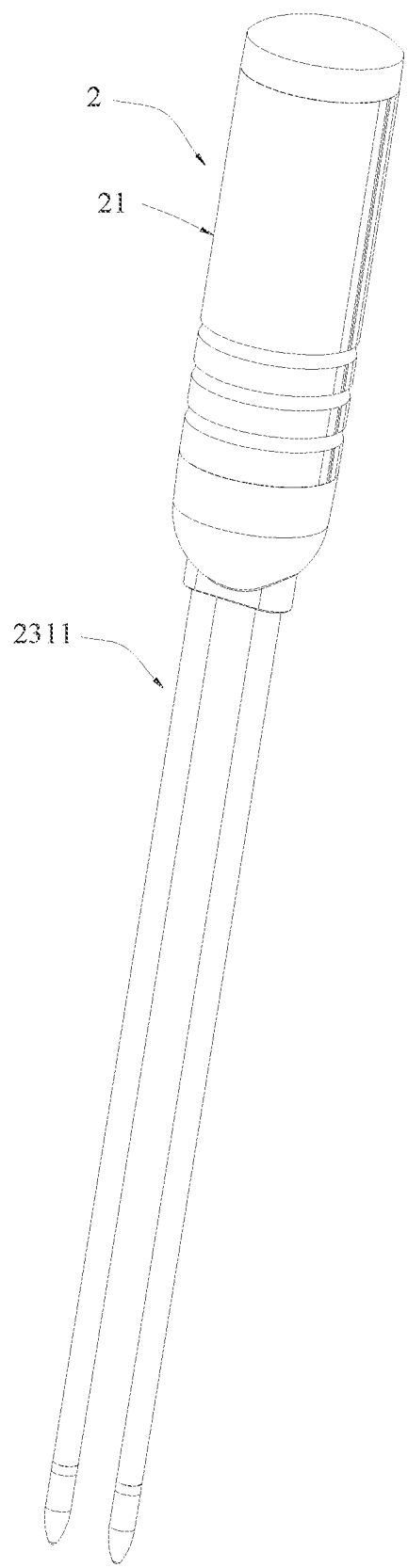
FIG. 3 is a three-dimensional diagram of a tester according to the present disclosure.

In this embodiment, as shown in FIG. 3, the soil moisture testing unit includes a testing probe 2311; the testing probe 2311 is arranged at one end of the tester main body 21; and one end of the testing probe 2311 is configured to be inserted into soil, and the other end of the testing probe 2311 is electrically connected to the first control circuit board 22. That is, the testing probe 2311 is inserted into the soil to test various data in the soil. The first control circuit board 22 is configured to test a soil moisture value, a soil PH value, a soil fertility content value, a soil nitrogen fertilizer content value, a soil potash fertilizer content value, and a soil phosphate fertilizer content value through the testing probe 2311. The probe in this embodiment can test one or more of the soil moisture, the soil pH value, the soil fertility content value, the soil nitrogen fertilizer content value, the soil potash fertilizer content value, and the soil phosphate fertilizer content value. One or more of the soil moisture data value, the soil pH data value, the soil fertility data value, the soil nitrogen fertilizer data value, the soil potash fertilizer data value, and the soil phosphate fertilizer data value tested by the tester are transmitted to the signal receiver 32 through the signal transmitter. The signal receiver 32 outputs the above tested data to the host unit 1. In this way, the host unit can receive the data tested by the tester 2 and display the data on the display screen of the host unit. The abovementioned soil moisture value, soil PH value, the soil fertility content value, the soil nitrogen fertilizer content value, the soil potash fertilizer content value, and the soil phosphate fertilizer content value can appear in the form of percentage. The tester can test the soil moisture, the PH value, the fertility, the nitrogen fertilizer, the potash fertilizer, and the phosphate fertilizer through the testing probe. When the testing probe 2311 is placed in the soil, the testing probe can measure a quantity of charges stored in the soil. The storable quantity of charges is directly proportional to a moisture content of the soil. Therefore, the moisture content of the soil can be calculated according to the measured quantity of charges. This information can be used to optimize irrigation and fertilization measures. The principle of the testing probe for testing the soil moisture, the PH value, the fertility, the nitrogen fertilizer, the potash fertilizer, and the phosphate fertilizer is of the prior art, and will not be elaborated here. In this embodiment, the soil moisture value is displayed on the host unit in the form of percentage. If the testing probe is not inserted into the soil, and the soil moisture value is zero. When the testing probe is inserted vertically into the soil, the testing probe automatically tests a current soil moisture. The receiver receives a signal and displays a current moisture percentage value of 41.

The soil moisture testing unit includes the testing probe 2311 and a soil moisture alarm. The soil moisture alarm is arranged inside the host unit main body and is electrically connected to the second control circuit board. If a default moisture value is set to be 10%, and the current soil moisture exceeds 10%, the soil moisture alarm will sound an alarm. Meanwhile, a setting button 17 and a toggle button are simultaneously pressed for three seconds to enter a customized moisture alarm value setting mode, within a range from 0% to 100%.

In this embodiment, as shown in FIG. 3, one end of the testing probe 2311 that is configured to be inserted into the soil is set to be conical, which is more convenient for the user to insert the testing probe 2311 into the soil. In this embodiment, it is preferred to include two testing probes 2311. The two testing probes 2311 can simultaneously test the conductivity and PH value, with higher accuracy and more accurate testing results. However, one probe can only test one indicator, usually the conductivity or the PH value, and there is a certain error in the testing result. Therefore, in this embodiment, the two testing probes 2311 are used. Whether there are two probes or there is one probe, the probe is of the prior art. The testing principles of the two probes and one probe will not be elaborated here.

In this embodiment, as shown in FIG. 1, the testing module 23 further includes the light testing unit 232. The light testing unit 232 mainly tests a light intensity. In the plant growth process, light serves as a main energy source for the survival of the plants and other organisms. The light intensity and light cycle elements affect the growth of the plants, and a magnitude of the light intensity and a duration will affect the growth cycle and physiological characteristics of the plants. Therefore, in this embodiment, the light testing unit 232 is arranged to improve the practicality of the soil testing instrument of the present disclosure.

The light testing unit 232 automatically tests the light intensity. The host unit receives a signal and displays a current light intensity value of 42, referring to a comparison table.

Figure 5:
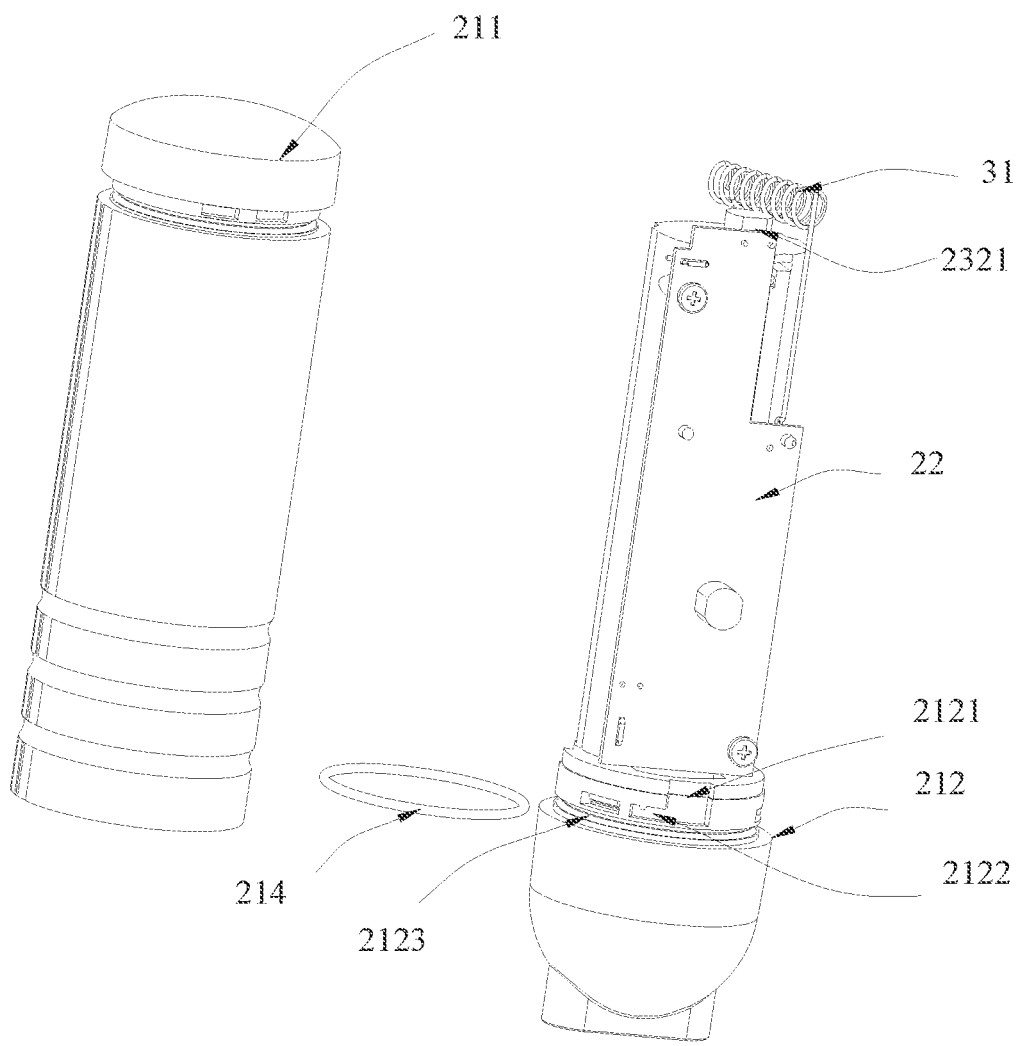
FIG. 5 is an exploded diagram of a tester according to the present disclosure.

In this embodiment, as shown in FIG. 4 to FIG. 5, the light testing unit 232 includes a photosensitive sensor 2321. The photosensitive sensor 2321 is configured to test an ambient light intensity to obtain the current light intensity value. The photosensitive sensor 2321 is arranged inside the tester main body 21, and the photosensitive sensor 2321 is electrically connected to the first control circuit board 22. The photosensitive sensor is a sensitive device that has a response or a conversion function to an external light signal or light radiation. The photosensitive sensor mainly includes: a photoelectric tube, a photomultiplier tube, a photoresistor, a photosensitive transistor, a solar cell, an infrared sensor, an ultraviolet sensor, an optical fiber type photoelectric sensor, a color sensor, a charge coupled device (CCD), a complex metal oxide semiconductor (CMOS) image sensor, and the like. A light sensor is one of the most productive and widely used sensors, which plays a very important role in automatic control and non electrical measurement technologies. In this embodiment, the photoresistor is preferred. When photons impact a junction, a current will be generated. Using the photoresistor has low production cost and can reduce the overall cost of the soil testing instrument.

In this embodiment, as shown in FIG. 4 to FIG. 5, the tester main body 21 includes a shell 211, a base 212, and a mounting column 213. The mounting column 213 is vertically mounted on the base 212; the shell 211 sleeves the mounting column 213; and the shell 211 is detachably covered at the base 212. The first control circuit board 22 is mounted on the mounting column 213. The tester main body 21 is in a long strip shape, which is equivalent to a grip, making it convenient for the user to hold and place the tester. The shell 211 is detachable on the base 212, making it convenient for the user to open the interior of the tester main body 21, repair internal components of the tester, and replace a storage power supply. In this embodiment, the mounting column 213 and the base 212 are preferably integrated to facilitate production and reduce mounting procedures.

In this embodiment, as shown in FIG. 6, a first sliding chute 2121 and a second sliding chute 2122 are arranged on the base 212; both the first sliding chute 2121 and the second sliding chute 2122 are arranged on a side wall of the base 212; a notch of the first sliding chute 2121 is formed towards the mounting column 213; the first sliding chute 2121 is communicated to the second sliding chute 2122; one end of the second sliding chute 2122 is vertically arranged at one end of the first sliding chute 2121 away from the mounting column 213; the shell 211 is provided with a convex block 2111 at one end close to the base 212; the convex block 2111 is arranged on an inner wall of the shell 211; when the shell 211 is mounted on the base 212, the convex block 2111 slides from the first sliding chute 2121 into the second sliding chute 2122; and then the shell 211 is rotated to clamp the convex block 2111 in the second sliding chute 2122. Such a clamped structure is more convenient for the user to assemble and disassemble the shell, which brings convenience to the user.

In this embodiment, as shown in FIG. 6, the tester main body 21 further includes a waterproof ring 214; a mounting slot 2123 is arranged around an outer side wall of one end of the base 212 that is mounted with the shell 211; the waterproof ring 214 is arranged in the mounting slot 2123; and when the shell 211 is covered at the base 212, the waterproof ring 214 is located inside the shell 211, so as to prevent water from entering a joint between the shell 211 and the base 212 to damage parts of the tester main body 21.

In this embodiment, a top of the shell 211 is made of a transparent material, and the photosensitive sensor 2321 is arranged near the top of the shell 211, which can better sense the light, so that the acquired data will be more accurate.

In this embodiment, as shown in FIG. 4 to FIG. 5, the tester 2 further includes a first storage power supply 24, and the first storage power supply 24 is configured for power storage. The first storage power supply 24 is mounted on the mounting column 213 to reduce a mounting space and make the tester 2 smaller. Furthermore, the first storage power supply 24 is electrically connected to the first control circuit board 22.

In this embodiment, as shown in FIG. 1, the testing module 23 further includes a temperature testing unit 233. The temperature testing unit 233 is configured to test a temperature value of an environment. Temperature has a certain impact on the growth of the plants. Therefore, in this embodiment, the temperature testing unit 233 is arranged to improve the practicality of the present disclosure. The temperature testing unit 233 uses a temperature sensor. The temperature sensor is arranged inside the tester and is electrically connected to the first control circuit board. An ambient temperature value of 43 is displayed on the screen of the host unit.

In this embodiment, as shown in FIG. 6, the signal transmitter 31 is arranged near a top of the tester main body 21.

Figure 8:
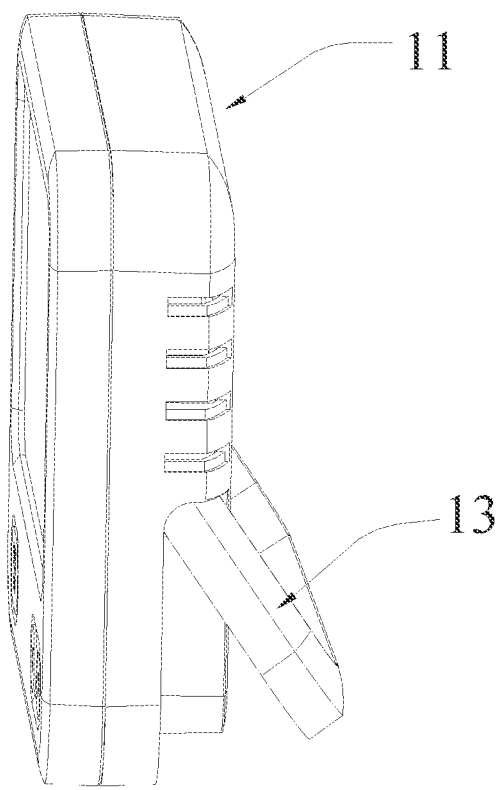
FIG. 8 is a diagram of usage states of a host unit and a support frame according to the present disclosure.

In this embodiment, as shown in FIG. 8, a support frame 13 is arranged on a back surface of the host unit main body 11, and the support frame 13 can be configured to support the host unit main body 1 on a platform, to facilitate use of the host unit.

In this embodiment, as shown in FIG. 6, the host unit 1 further includes a second storage power supply 14 and the display screen 15; the display screen 15 is arranged on one side of the host unit main body 11; the second storage power supply 14 is arranged inside the host unit main body 11; and both the second storage power supply 14 and the display screen 15 are electrically connected to the second control circuit board 12. The second storage power supply 14 is configured for power storage.

Figure 7:
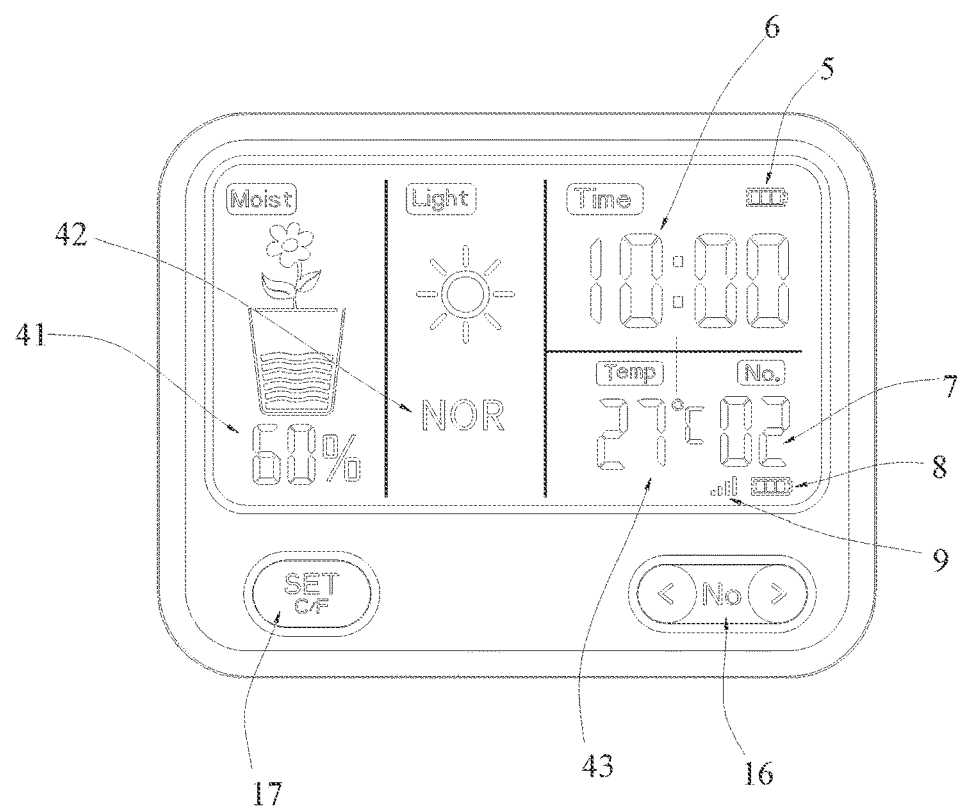
FIG. 7 is a schematic diagram of displaying of a display screen of a host unit according to the present disclosure.

In this embodiment, as shown in FIG. 7, the display screen 15 can display the tested data tested by the tester 2, a power level 5 and time 6 of the second storage power supply, a quantity 7 of connected testers, a power level 8 of the first storage power supply, and signal strength 9 of the tester. It is convenient for the user to observe these data. The tested data includes the moisture percentage value of 41, the light intensity value of 42, and the ambient temperature value of 43.

In this embodiment, as shown in FIG. 7, the host unit 1 further includes a toggle button 16 and a setting button 17; both the toggle button 16 and the setting button 17 are electrically connected to the second control circuit board 12; the toggle button 16 and the setting button 17 are arranged on the host unit main body 11 and are located on the same side of the display screen 15; there are two or more testers 2; the two or more testers 2 can be connected to the host unit 1 through the wireless communication; the display screen 15 can display a quantity of display testers 2 connected to the host unit 1; the quantity of the testers 2 connected to the host unit 1 is switched by the toggle button 16, and the tested data corresponding to the testers 2 is switched simultaneously; and the setting button 17 is configured to set the time, or set the unit of the temperature mentioned above. In this embodiment, a long press is made to the setting button for three seconds to enter time setting. A twenty-four hours system or a twelve hours system is selected to enter minute setting. The setting button is pressed for three seconds for confirmation to exit the time setting.

A specific usage method of the soil testing instrument in this embodiment is as follows: Before use, make sure to mount a battery in the receiver for self inspection (the device needs to be close within 5 meters) and then mount a battery in the transmitter for automatic matching.

When there are a plurality of transmitters, the battery is first mounted in the receiver for self inspection, and then batteries are mounted in the transmitters one by one for matching, and numerical label pasters are adhered. This makes it convenient for the receiver to display device numbers that are consistent with the numerical label pasters of the transmitters.

The transmitters are added separately: After the transmitters are adhered with the label pasters in sequence according to existing numbers and are mounted with the batteries, the transmitters are automatically matched.

The receiver is added separately: The batteries of all the transmitters need to be removed in advance. The receiver is first mounted with the battery for self inspection, and then the transmitters are mounted with the batteries one by one according to the numerical labels for automatic matching.

Note: The receiver and the transmitter will be automatically matched after being mounted with the batteries and started up. If a matching order is incorrect, it is not convenient for management.

Method 1: The toggle button of the host unit can be press for 10 seconds for resetting (all displayed contents are cleared), and then matching is performed again.

Method 2: The numerical label pasters are rearranged by the tester according to the numbers of the receiver end.

The foregoing description is merely illustrative of the preferred embodiments of the present disclosure and is not intended to limit the present disclosure, but it is intended that any modifications, equivalents, substitutions, and modifications made within the spirit and principles of the present disclosure be embraced within the scope of the present disclosure.

What is claimed is:

1. A soil testing instrument, wherein the soil testing instrument comprises a host unit and a tester;

the tester is connected to the host unit through wireless communication; the wireless communication connection is configured to achieve wireless communication between the host unit and the tester; and the tester transmits tested data to the host unit through the wireless communication, the tested data comprises soil moisture information and ambient light intensity information, the host unit comprises a display screen, a second control circuit board and a host unit main body, and the display screen is configured to display the soil moisture information and the ambient light intensity information, wherein the host unit further comprises a toggle button; the toggle button is electrically connected to the second control circuit board; the toggle button is arranged on the host unit main body and is located on a side of the display screen; there are two or more testers; the two or more testers are connected to the host unit through the wireless communication; the display screen is also configured to display a quantity or a number of the two or more testers connected to the host unit; the quantity or the number displayed by the display screen is able to be switched by the toggle button, the soil moisture information and the ambient light intensity information corresponding to one tester of the two or more testers is switched simultaneously.

2. The soil testing instrument according to claim 1, wherein the wireless communication comprises a signal transmitter and a signal receiver; the signal receiver is arranged on the host unit and is electrically connected to the host unit; the signal transmitter is arranged on the tester and is electrically connected to the tester; the data tested by the tester is transmitted to the signal receiver through the signal transmitter; the signal receiver transmits the received data to the host unit.

3. The soil testing instrument according to claim 2, wherein both the signal transmitter and the signal receiver are antennas.

4. The soil testing instrument according to claim 3, wherein the tester comprises a tester main body, a first control circuit board, and a testing module; the first control circuit board and the signal transmitter are both arranged inside the tester main body; the testing module is arranged on the tester main body; the testing module and the signal transmitter are electrically connected to the first control circuit board; the signal receiver and the second control circuit board are arranged inside the host unit main body; the signal receiver and the display screen are electrically connected to the second control circuit board; the first control circuit board acquires the tested data through the testing module; the tested data acquired by the first control circuit board is then transmitted to the signal receiver through the signal transmitter; and the signal receiver transmits the received tested data to the host unit.

5. The soil testing instrument according to claim 4, wherein the testing module comprises one or more of a soil moisture testing unit, a PH value testing unit, a fertility testing unit, a nitrogen fertilizer testing unit, a potash fertilizer testing unit, and a phosphate fertilizer testing unit.

6. The soil testing instrument according to claim 5, wherein the soil moisture testing unit comprises at least one testing probe; the soil testing instrument comprises a length direction, the at least one testing probe is arranged at and connected to one end of the tester main body along the length direction, the signal transmitter is disposed at the other end opposite to the one end of the tester main body; one end of the at least one testing probe is configured to be inserted into soil, and the other end of the at least one testing probe is electrically connected to the first control circuit board; the first control circuit board tests and obtains one or more of a soil moisture value, a soil PH value, a soil fertility content value, a soil nitrogen fertilizer content value, a soil potash fertilizer content value, and a soil phosphate fertilizer content value through the testing probe; and the end of the at least one testing probe that is configured to be inserted into the soil is conical.

7. The soil testing instrument according to claim 6, wherein the at least one testing probe comprises two testing probes parallel to each other, the two testing probes are electrically connected to the first control circuit board, and the end of the testing probe is configured to be inserted into the soil is conical.

8. The soil testing instrument according to claim 5, wherein the soil moisture testing unit comprises a soil moisture alarm, the soil moisture alarm is arranged inside the host unit main body and is electrically connected to the second control circuit board, if a default moisture value is set to be a predetermined value, and the current soil moisture exceeds the predetermined value, the soil moisture alarm will sound an alarm.

9. The soil testing instrument according to claim 4, wherein the testing module further comprises a light testing unit, the light testing unit comprises a photosensitive sensor; the photosensitive sensor is configured to test an ambient light to obtain the ambient light intensity information; the photosensitive sensor is arranged on the tester main body; and the photosensitive sensor is electrically connected to the first control circuit board.

10. The soil testing instrument according to claim 9, wherein the tester main body comprises a shell, a base, and a mounting column; the mounting column is mounted on the base along the length direction; the shell sleeves the mounting column; the shell is detachably covered at the base; the signal transmitter is located adjacent to a top end of the mounting column far away from the base, and the first control circuit board is mounted on the mounting column.

11. The soil testing instrument according to claim 10, wherein the tester main body further comprises a waterproof ring; a mounting slot is arranged around an outer side wall of one end of the base that is mounted with the shell; the waterproof ring is arranged in the mounting slot; and when the shell is covered at the base, the waterproof ring is located inside the shell.

12. The soil testing instrument according to claim 10, wherein a top of the shell is made of a transparent material, and the photosensitive sensor is arranged near the top of the shell.

13. The soil testing instrument according to claim 10, wherein the tester further comprises a first storage power supply; the first storage power supply is mounted on the mounting column; and the first storage power supply is electrically connected to the first control circuit board.

14. The soil testing instrument according to claim 13, wherein the host unit further comprises a second storage power supply and the display screen; the display screen is arranged on one side of the host unit main body; the second storage power supply is arranged inside the host unit main body; and both the second storage power supply and the display screen are electrically connected to the second control circuit board.

15. The soil testing instrument according to claim 14, wherein the host unit further comprises a setting button; both the toggle button and the setting button are electrically connected to the second control circuit board; the toggle button and the setting button are arranged on the host unit main body and are located on the same side of the display screen; and the setting button is configured to set the time.

16. The soil testing instrument according to claim 4, wherein the testing module further comprises a temperature testing unit, and the temperature testing unit is configured to test a temperature of an environment to obtain ambient temperature information.

17. The soil testing instrument according to claim 4, wherein a support frame is arranged on a back surface of the host unit main body opposite to the display screen, and the support frame is configured to support the host unit main body on a platform.

18. A soil testing instrument, wherein the soil testing instrument comprises a host unit and a tester; the tester is connected to the host unit through wireless communication; the wireless communication connection is configured to achieve wireless communication between the host unit and the tester; and the tester transmits tested data to the host unit through the wireless communication, wherein the wireless communication comprises a signal transmitter and a signal receiver; the signal receiver is arranged on the host unit and is electrically connected to the host unit; the signal transmitter is arranged on the tester and is electrically connected to the tester; the data tested by the tester is transmitted to the signal receiver through the signal transmitter; the signal receiver transmits the received data to the host unit; and the host unit displays the tested data through a display screen of the host unit, wherein the tester comprises a tester main body, a first control circuit board, and a testing module; the first control circuit board and the signal transmitter are both arranged inside the tester main body; the testing module is arranged on the tester main body; the testing module and the signal transmitter are electrically connected to the first control circuit board; the host unit comprises a host unit main body and a second control circuit board; the signal receiver and the second control circuit board are arranged inside the host unit main body; the signal receiver is electrically connected to the second control circuit board; the first control circuit board acquires the tested data through the testing module; the tested data acquired by the first control circuit board is then transmitted to the signal receiver through the signal transmitter; and the signal receiver transmits the received tested data to the host unit, wherein the tester main body comprises a shell, a base, and a mounting column; the mounting column is vertically mounted on the base; the shell sleeves the mounting column; the shell is detachably covered at the base; and the first control circuit board is mounted on the mounting column, wherein a first sliding chute and a second sliding chute are arranged on the base; both the first sliding chute and the second sliding chute are arranged on a side wall of the base; a notch of the first sliding chute is formed towards the mounting column; the first sliding chute is communicated to the second sliding chute; one end of the second sliding chute is vertically arranged at one end of the first sliding chute away from the mounting column; the shell is provided with a convex block at one end close to the base; the convex block is arranged on an inner wall of the shell; when the shell is mounted on the base, the convex block slides from the first sliding chute into the second sliding chute; and then the shell is rotated to clamp the convex block in the second sliding chute.

19. A soil testing instrument, wherein the soil testing instrument comprises a host unit and a tester;

the tester is connected to the host unit through wireless communication; the wireless communication connection is configured to achieve wireless communication between the host unit and the tester; and the tester transmits tested data to the host unit through the wireless communication, the tested data comprises soil moisture information and ambient light intensity information, the host unit comprises a display screen and a host unit main body, and the display screen is configured to display the soil moisture information and the ambient light intensity information, wherein the tester further comprises a first storage power supply, the host unit further comprises a second storage power supply and the display screen; the second storage power supply is arranged inside the host unit main body, wherein the display screen is also configured to display a signal strength of the wireless communication, a power level of the first storage power supply, and a power level of the second storage power supply of the one tester of the two or more testers.

20. The soil testing instrument according to claim 19, wherein the display screen is arranged on one side of the host unit main body, the display screen is also configured to display current time information, ambient temperature information, the soil moisture information comprises at least one first character, a first pattern and the soil moisture value, the ambient light intensity information comprises at least one second character, a second pattern and an light intensity level, the display screen is also configured to display a power level of the second storage power supply.

* * * * *